United States Patent [19]

Dragan

[11] Patent Number: 5,061,179
[45] Date of Patent: Oct. 29, 1991

[54] MANUAL EXTRUDER AND CARTRIDGE HAVING INTERLOCKING BEARING SURFACES

[76] Inventor: William B. Dragan, 85 Burr St., Easton, Conn. 06612

[21] Appl. No.: 577,019
[22] Filed: Sep. 4, 1990
[51] Int. Cl.[5] ............................................. A61C 5/04
[52] U.S. Cl. .................................................... 433/90
[58] Field of Search ................... 433/89, 90; 604/232, 604/233, 234, 235, 275; 222/327

[56] References Cited

U.S. PATENT DOCUMENTS

| | | | |
|---|---|---|---|
| 3,076,455 | 2/1963 | McConnaughey | 604/232 |
| 3,220,412 | 11/1965 | McConnaughey | 604/235 |
| 3,581,399 | 6/1971 | Dragan | 433/90 |
| 4,198,756 | 4/1980 | Dragan | 433/90 X |
| 4,295,828 | 10/1981 | Rudler | 433/90 |
| 4,330,280 | 5/1982 | Dougherty et al. | 433/90 |
| 4,384,853 | 5/1983 | Welsh | 433/90 |

FOREIGN PATENT DOCUMENTS

MU5701465  6/1979  Brazil .

Primary Examiner—John J. Wilson
Assistant Examiner—Jeffrey A. Smith
Attorney, Agent, or Firm—Arthur T. Fattibene; Paul A. Fattibene

[57] ABSTRACT

A manual extruder and cartridge having interlocking or mating bearing surfaces. The front end or tip portion of a dental material manual extruder is formed with flexible sidewalls to define a snap or friction fit chamber adapted to receive a cartridge containing a supply of dental material. The rear of the chamber is formed with an angled shoulder or bearing surface. A cartridge, adapted to be snap fit, press fit, or friction fit into the chamber has a flange having complementary angled surface so that when a viscous dental material is extruded, the large forces generated cause the angled surfaces of the flange and adjacent shoulder to interlock and prevents the flexible sidewalls of the barrel from separating apart and prohibits the cartridge from becoming unintentionally detached from the manual extruder or being wedged between the flexible sidewalls.

10 Claims, 1 Drawing Sheet

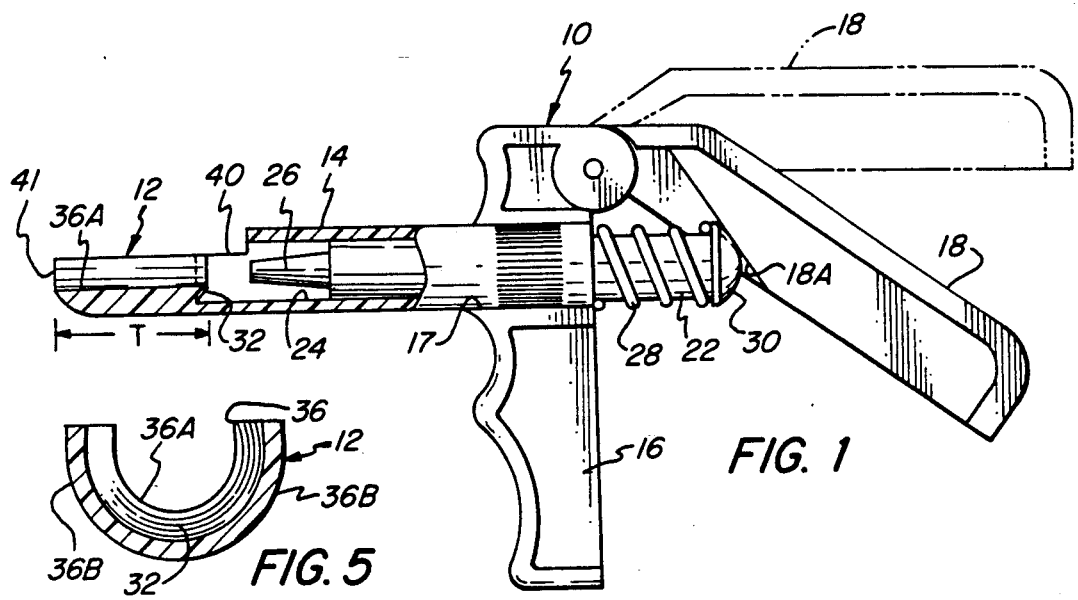
FIG. 1
FIG. 5
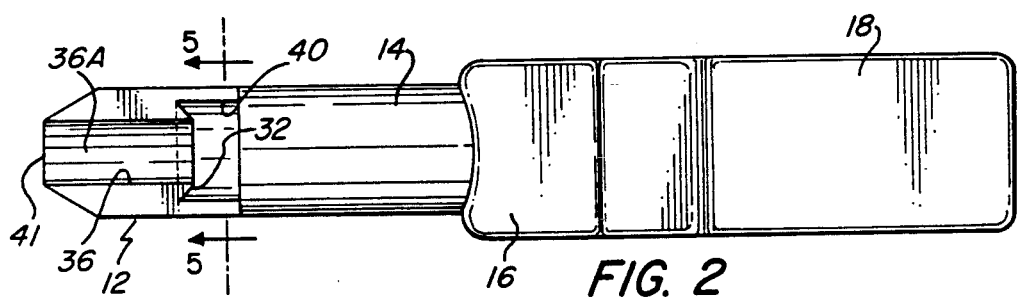
FIG. 2
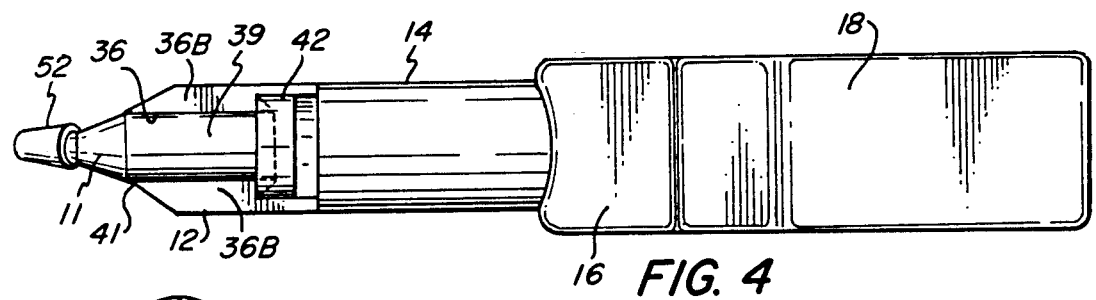
FIG. 4
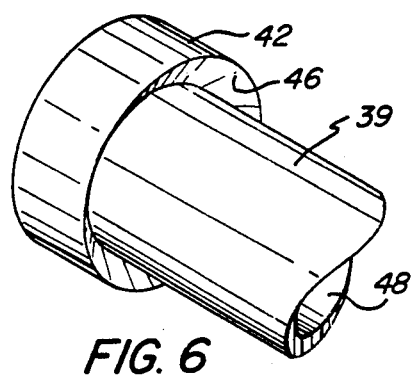
FIG. 6
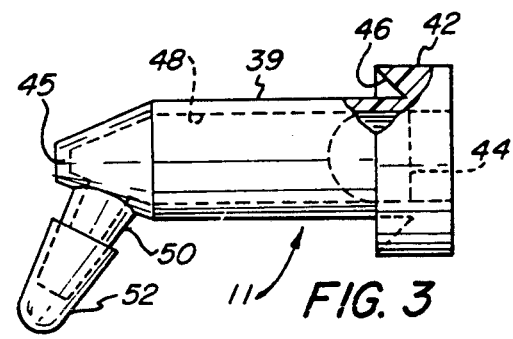
FIG. 3

MANUAL EXTRUDER AND CARTRIDGE HAVING INTERLOCKING BEARING SURFACES

FIELD OF THE INVENTION

This invention relates generally to a dental device for the placement of dental materials, and more particularly to a dental syringe device having an improved barrel front end portion and an associated cartridge having complementary interlocking surfaces.

BACKGROUND OF THE INVENTION

As the dental practice advances with the discovery of new filling materials, there developed a need for a new system to place such materials in a tooth. The earliest known delivery system for use with composite resin type dental materials is disclosed in U.S. Pat. No. 3,581,399 issued to Dragan on June 1, 1971. Therein disclosed is a manual extruder for positioning viscous dental material within a prepared tooth. A further improved delivery system is disclosed in U.S. Pat. No. 4,198,756 to Dragan dated April 22, 1980. The device disclosed therein provides a mechanical advantage for the controlled dispensing of the viscous dental material. These devices permit improved dental filling techniques, in that the viscous material is placed in the tooth cavity from the bottom up; to result in the elimination of voids in the tooth filling, which occurred in the previous technique of using a spatula to pack the viscous dental material from the exterior to the interior of the tooth.

As might be expected, refinements have been made to the initial concepts disclosed in the above mentioned Dragan patents. One such refinement is disclosed in U.S. Pat. No. 4,295,828 issuing to Rudler on Oct. 20, 1981. Therein disclosed is a manual extruder very similar to the initial Dragan U.S. Pat. No. 4,198,756, but differing therefrom in that the front end of the barrel is provided with a hinging section for loading and locking a cartridge in place at the front end of the barrel.

It was recognized early on that a syringe having a barrel construction with a snap fit front end construction would facilitate the positioning of a cartridge to the front end so as to provide for easy and rapid placement of a cartridge in the syringe device. Such snap fit front end barrel constructions are disclosed in U.S. Pat. Nos. 3,076,455 and 3,220,412 to McConnaughey dated Feb. 5, 1963 and November 1965 respectively. McConnaughey teaches a syringe device with a snap fit to hold a cartridge onto the end of a barrel by lateral movement relative to a side opening that is accomplished by momentarily distorting the holder to widen the side opening through which the cartridge is inserted to provide the pressed or snap fit. McConnaughey, in the U.S. Pat. No. 3,076,455, FIG. 12 thereof, also discloses a snap fit channel 80 having an internal groove or depression 82 for receiving the flange or bead 78 of the cartridge to retain the cartridge at the front end of a barrel portion and to prevent axial displacement of the cartridge. Brazilian patent application MU5701465 filed Nov. 22, 1977 and published July 3, 1979 discloses a similar "snap or pressed" fit front end construction. The snap fit with undercut groove for retaining a cartridge as applied to a manual extruder for dental materials are thus well known. Such snap fit front end barrel constructions have also been utilized in other dental syringe devices as disclosed in U.S. Pat. No. 4,330,280 and U.S. Pat. No. 4,384,853. These latter two U.S. patents disclose a manually operable dental syringe for cartridge containing dental material similar to the dental syringe of U.S. Pat. No. 4,198,756, but utilizing a front end barrel construction having a snap fit as suggested by McConnaughey. The snap fit construction disclosed in said latter two patents is provided with an undercut groove to receive the flanged end of the cartridge wherein the sidewalls of the groove at the upper edges have limited flexibility and spaced apart slightly less than the diameter of the cartridge flange to effect a limited snap connection of the cartridge flange within the undercut groove of the holder.

While these modifications attempted to facilitate the easy placement of a cartridge in a manual extruder, problems with respect thereto have been noted. For example, the inherent flexibility necessary to provide for a snap fit to facilitate attachment of a cartridge, e.g. as disclosed in U.S. Pat. Nos. 4,330,280 and 4,384,853, results in the susceptibility of the side walls of the snap fit compartment or groove to be forcibly spread apart during use if an excessive pressure is applied during an extruding operation. This may well cause the cartridge to be literally shot from the barrel during an extruding operation. This is particularly troublesome when very high extruding pressures are required to be applied to extrude the viscous dental material necessary with such dental cartridges. This is caused by the flange of the cartridge acting as a wedge to force the flexible sidewalls of the snap fit front end to unintentionally spread apart sufficient to cause the cartridge to be forced from its compartment or groove. This is particularly undesirable in a dental procedure when the cartridge at the front end of the syringe is placed in the oral cavity. Should such cartridge be dislodged from the syringe, it can be accidentally inhaled or swallowed by the patient, thereby causing serious harm to the patient. Also, wear which normally occurs in use may also cause the cartridge to become loosely held by the syringe to result in unintentional separation of the cartridge during an extruding operation.

OBJECTS

An object of this invention is to provide an improved snap fit front end barrel construction for use in a dental syringe in which any unintentional separation of the cartridge from the syringe device is positively resisted.

Another object is to provide an improved snap fit barrel construction and cartridge construction having an interlocking arrangement for positively retaining a cartridge which becomes more positive as the extruding pressure is increased.

Another object is to provide a syringe device with a snap fit front end barrel construction cooperatively associated with a cartridge to prohibit any unintentional separation of the cartridge from the barrel during an extruding operation.

Another object is to provide a dental syringe device with a front end barrel construction having flexible side walls to facilitate a snap fit retention of a cartridge therein and constructed to prohibit any outward flexing of the sidewalls during an extruding operation so as to prohibit any unintentional separation of the cartridge therefrom.

SUMMARY OF THE INVENTION

The foregoing objects, object features, and advantages are attained by a syringe device, e.g. a dental syringe having a barrel formed with a snap fit front end construction defined by flexible side wall portions adapted to retain a tubular or a cylindrically walled cartridge. The arrangement is such that the flexible side walls at the front end of the barrel are provided with a side opening whereby the distance between the edges of the side opening is less than the diameter of the tubular cartridge to be received thereby. Thus, the side or longitudinal opening defines a chamber having flexible side walls of a sufficient length to encompass a portion of the cartridge tubular body when the cartridge is positioned therein. At the rear portion of the chamber, there is provided a shoulder which, according to this invention, is formed with an angular or inclined bearing surface which is co-extensive to the circumferential portion of the shoulder at the inner end of the chamber. The cartridge to be received within the compartment is provided with a laterally extending flange or collar which is adapted to abut or engage the shoulder. In accordance with this invention, the abutting edge of the collar or flange of the cartridge is provided with an angularly disposed bearing surface to complement the inclined bearing surface of the shoulder. The arrangement is such that when pressure is applied to the end of the cartridge during an extruding operation, the flange of the cartridge is forcibly urged against the shoulder of the snap fit compartment, so that the inclined complementary surfaces of the flange or collar of the cartridge engages and mates with the inclined surface of the shoulder to form a positive interlocking connection which will positively resist any tendency of the flexible sidewalls of the snap fit compartment to spread laterally outward; thereby prohibiting any unintentional release of the cartridge from its snap fitting chamber at the front end of the syringe barrel. The inclination of the mating surfaces of the collar and shoulder are such that the greater the pressure that is applied to the cartridge, the greater becomes the interlocking forces that resist any lateral or outward spreading of the flexible sidewalls of the snap fit compartment or chamber.

FEATURES

A feature of this invention is to provide for complementary interlocking surfaces between the collar or flange of a cartridge and the adjacent shoulder of a snap fit compartment of a syringe device to prevent any unintentional outward spreading of the flexible sidewalls of the snap fit compartment during an extruding operation.

Another feature resides in providing a syringe device having a snap fit compartment formed by a rear shoulder having an angularly inclined, concavely, disposed wall surface extending circumferentially about said shoulder.

Another feature resides in the provision of a cartridge having a laterally outwardly extending flange provided with an angularly disposed wall surface extending forwardly toward the shoulder of the snap fit compartment formed at the front end of the syringe barrel.

It is yet another feature of the present invention to provide a dental syringe that requires less force to position the cartridge between the flexible sidewalls thereof that insures a positive retention of the cartridge, even when large extrusion forces are required.

Another feature of the present invention is that the cartridge flange has an angled bearing surface which mates with an angled bearing surface at the barrel end wall.

Another feature of the present invention is to provide the barrel end wall and the flange of a cartridge with interlocking mating surfaces so that when an extruding pressure is applied to the cartridge, the cartridge resists any tendency of the sidewalls of the barrel to spread apart.

BRIEF DESCRIPTION OF THE DRAWINGS

FIG. 1 is a partial cross-section of a syringe device embodying the present invention.

FIG. 2 is a top view of FIG. 1.

FIG. 3 is a side view of a cartridge of the present invention.

FIG. 4 is a top view of the manual extruder or syringe of the present invention with the cartridge in position therein.

FIG. 5 is a cross section taken along line 5—5 in FIG. 2.

FIG. 6 is a partial perspective view of the cartridge illustrated in FIG. 3 illustrating the improvement therein.

DETAILED DESCRIPTION OF THE PREFERRED EMBODIMENTS

FIG. 1 illustrates the syringe device 10 embodying the present invention. The illustrated syringe or manual extruder 10 includes a barrel 14 and an associated handle means which includes a pivoting handle or lever portion 18 attached to the upper end of a finger grip portion 16 which is connected to a cylindrical barrel 14. The barrel 14 has a front end portion 12 provided with a snap fit compartment, as will be hereinafter described. The finger grip 16 has a barrel opening 17 therein through which barrel 14 is securely positioned or otherwise connected. If desired, the barrel 14 may be integrally formed with the finger grip 16, e.g. by molding. The lever handle 18 can be moved upward as indicated by the dot-dash position, in FIG. 1, to permit easy insertion of plunger 22 into and out the barrel bore 24 to facilitate cleaning. Plunger 22 has a forward plunger tip 26 attached to one end. The other end of plunger 22 is provided with a plunger head 30. A spring 28 is retained along the plunger 22 between the front handle or finger grip 16 and the plunger head 30. Plunger head 30 is adapted to slide on a bearing surface 18A formed on the lever handle 18. Therefore, when lever handle 18 is manually squeezed closer to front or finger grip 16, the plunger 22 is forced forward. The lever handle 18 thus provides a mechanical advantage in extruding the viscous dental material from a cartridge in the operative position of the syringe 10. Such mechanical advantage is required due to the very viscous nature of the dental material required to be extruded from the cartridge.

As shown, the bore 24 of the barrel 14 terminates at its front end by an inturned shoulder 32 to define an end wall. The end wall is provided with a width or thickness "T" sufficient to define a seat or compartment 36A to retain a sufficient portion of the cartridge body 39.

In accordance with this invention, the front end of the barrel 14 is formed of a flexible material and is provided with a front opening 41 and a longitudinally extending cut out portion as indicated at 36. However, the front end of the barrel 14 could be rigid and the cartridge body 39 could be made flexible, or both could be made flexible. The cut out portion 36 defines a forwardly extending snap fit compartment or chamber 36A having opposed flexible side walls 36B–36B. In the illustrated embodiment, the longitudinal slot 36 is formed along the upper surface of the barrel 14 at the front end and which extends slightly beyond the rear of the shoulder 32. The width of the slot 36 is less than the diameter of the body portion 39 of the cartridge adapted to be retained within the snap fit compartment 36A. It will be understood that the length of the compartment 36A is sufficient to engage a sufficient portion of the cartridge body portion 39 to ensure stability of the cartridge within the compartment 36A.

The rearward portion of the compartment 36A is defined by the shoulder or end wall 32, which is angularly disposed as best noted in FIG. 1 Thus, as shown, the compartment 36A has a diameter substantially equal to the diameter of the cartridge body portion 39 and less than the diameter of the bore 24. The diameter of the collar or flange 42 of the cartridge 11 is less than the diameter of the bore 24 and greater than the diameter of the cartridge body 39. With the construction described, no undercut groove is required to retain the cartridge flange 42 by a snap fit, as the flange 42 of the cartridge 11 is disposed within the bore 24 of the barrel 14 to the rear of shoulder 32. The shoulder 32 is defined by an inclined end wall surface 32 co-extensive to the circumference of the shoulder or end wall 32 to define a conical surface. The longitudinal slot 36 extends from the front opening 41 and rearwardly of the shoulder 32 to provide a rear opening 40 adapted to receive the diameter of the cartridge collar 42 as will be hereinafter described. Thus, the opening 40 is sized so as to be slightly greater than the diameter of the flange 42.

FIG. 2 and FIG. 5 better illustrates the barrel tip or end portion 12. In FIG. 2, the flexible sidewalls 36B-36B can easily be seen. The sidewalls are made flexible so as to flex apart sufficiently to permit the body 39 of the cartridge 11 to be snap fitted into the compartment 36A through the side opening 36. The sidewalls 36B thus provide a snap fit, press fit, or friction fit retention means to retain the cartridge 11 when placed therein. With the present invention, the sidewalls 36B-36B can be made more flexible than thought previously possible and still securely hold the cartridge in place even when the large extrusion forces are applied as will be described. This is advantageous in that the dentist can more easily insert and remove cartridges at the front end of the barrel.

FIGS. 3 and 6 illustrates a cartridge 11 for use with the manual extruder 10 as illustrated in FIGS. 1 and 2. The cartridge 11 includes a body portion 39 having a circular flange 42 about the open end thereof. The flange 42 is formed with an inclined complementary surface 46 to provide a female conical surface adapted to mate with the inclined bearing or conical male surface 32 forming the shoulder or end wall of the bore 24, that defines the rear of the snap fit compartment 36A. The flange conical or bearing surface 46 is angularly disposed to receive and mate with the angular or conical surface 32 of the shoulder. The body portion 39 of the cartridge defines a reservoir for containing a supply of dental restorative material. The open end of the body portion 39 for receiving the dental material is adapted to be sealed by a displaceable plug or piston 44. Opposite the open end, the body portion 39 is provided with a closed end 45. At the closed end is a discharge nozzle 50. Nozzle 50 is angularly disposed with respect to the longitudinal axis of reservoir 48 so as to permit easy placement of dental filling material contained within cartridge 11. A sealing cap 52 may be placed over nozzle 50 preventing any contamination of the dental material contained within the cartridge 11 when not in use. The cartridge 11 can be made opaque to accommodate light activated dental material. Additionally, the cap 52 or plug 44 can be color-coded to indicate the type or shade of material contained within cartridge 11. Other identifying indicia can also be used.

FIG. 4 illustrates the cartridge 11, positioned within the manual extruder 10. As can be appreciated, the body portion 39 of cartridge 11 is forced or snap fitted through the side opening 36 into the compartment 36A formed at the front end of the barrel. The diameter of body portion 39 is made slightly larger than the opening 36. Thus, in placing the cartridge into compartment 36, the flexible sidewalls 36B-36B are momentarily spread apart, causing the cartridge 11 to be snapped or pressed in place within the compartment 36A. Additionally, the body portion 39 can also be made to momentarily deform inward facilitating the snap-fit. The circumferential barrel portion 14 to the rear of the compartment 36A is slightly larger than the diameter of flange 42 to receive the flange. As the manual extruder is operated, plunger tip 26 is forced against plug or piston 44 to extrude the material contained within the reservoir of the capsule. In doing so, the applied pressure on the cartridge causes the bearing surface 46, 32 of the collar 42 and the end wall to mate and interlock. As a result of this mating or interlocking action, the flexible sidewalls 36B-36B are prevented from being spread apart, regardless of the amount of force required to extrude the viscous dental material.

This is because the inclination of the complementary interlocking surfaces 32 and 46 is such that the greater the force applied on the end of the cartridge, the greater becomes the force that resists the lateral spreading of the flexible wall portions 36B-36B. Therefore, cartridge 11 cannot be forced out of the barrel tip portion 12 despite the flexibility of the sidewalls 36B-36B; as the bearing surface 46 of the collar or flange 42 will prohibit the flexible sidewalls 36B-36B from being spread apart.

The bearing surface 46 can be angularly disposed by less than 30 degrees.

With the construction described, any unintentional separation of the cartridge 11 from its snap fit compartment 36 due to lateral outward spreading of the flexible wall under axial pressure applied to the cartridge during an extruding operation is prohibited.

As should now be appreciated, the present invention greatly facilitates the insertion and removal of a cartridge by a dentist. This easy insertion and removal is not compromised by the risk of the cartridge becoming unintentionally detached from the manual extruder, even during the very high forces required to extrude the viscous dental material. Thus, accidental separation of the cartridge which can cause considerable and serious injury to a patient is avoided.

Although the preferred embodiment has been illustrated and described, it will be obvious to those skilled in the art that various modifications and variations may be made without departing from the spirit and scope of this invention.

What is claimed is:

1. A manual extruding system for use in placing dental materials comprising
    a dental syringe and an associated disposable cartridge,
    said dental syringe having a barrel having a chamber formed at the front end thereof for retaining said cartridge thereat, said chamber having a front opening and a longitudinal slot extending rearwardly of said front opening to define a side breech opening, said chamber having flexible side wall portions, an inturned shoulder disposed internally of said barrel to define the rear end of said chamber, said cartridge having a body portion and a laterally extending flange connected to said body portion, a plunger reciprocally mounted in said barrel, and complimentary interlocking means on said shoulder and flange for effecting a positive interlock between said shoulder and said flange to prohibit any outwardly spreading of said flexible side walls of said chamber when a force is applied to said cartridge by said plunger during an extruding operation, wherein said interlocking means includes complimentary inclined surfaces formed on said shoulder and said flange.

2. A manual extruding system for use in placing dental materials comprising a dental syringe and an associated disposable cartridge, said dental syringe having a barrel having a chamber formed at the front end thereof for retaining said cartridge thereat, said chamber having a front opening and a longitudinal slot extending rearwardly of said front opening to define a side breech opening, said chamber having flexible side wall portions, an inturned shoulder disposed internally of said barrel to define the rear end of said chamber, said cartridge having a body portion and a laterally extending flange connected to said body portion, a plunger reciprocally mounted in said barrel, and means on said shoulder and said flange for interlocking said flange and shoulder by structural forces other than the frictional forces between said shoulder and said flange to prohibit any outwardly spreading of said flexible side walls of said chamber when a force is applied to said cartridge by said plunger during an extruding operation, said interlocking means includes an inclined surface formed on said shoulder, said shoulder having a surface inclined rearwardly of said chamber, and said complimentary flange having a surface inclined forwardly and outwardly of said body portion.

3. A manual extruding system for use in placing dental materials comprising a dental syringe and a readily disposable cartridge for use therewith, said cartridge being adapted to contain a predetermined amount of dental material, said syringe including an elongated barrel having a front end portion defining a front opening and a rear end portion, said barrel having a bore extending therethrough, a longitudinally extending slot formed at said front end and extending rearwardly of said front opening to define a chamber having a side opening at said front end portion, said chamber having flexible side walls, an inturned flange defining a shoulder disposed between said chamber and said bore to delineate the said chamber from said bore, said cartridge having a body portion defining a reservoir for containing the dental material, a laterally extending flange disposed at one end of said body portion and a discharge nozzle connected to the other end of said body portion, said slot defining a side opening having a width which is less than the diameter of said cartridge body portion whereby said cartridge is fitted through said side opening and retained in said chamber, a plunger reciprocally mounted in the bore of said barrel, interlocking means formed on the flange and said shoulder whereby upon the application of a force on said plunger causes said flange to interlock with said shoulder by structural forces other than the frictional forces between said shoulder and said flange to preclude any outward spreading of said flexible side walls of said chamber, said interlocking means comprises a shoulder having a male conical surface and said flange having a complementary female conical surface for receiving said male conical surface when an axial is applied to said cartridge during an extruding operation.

4. A manual extruding system for use with dental materials comprising:

a barrel, said barrel having a front and rear end, said barrel having a longitudinally extending opening adjacent said front end, said opening extending axially partially along said barrel and at a radial depth less than the radius of said barrel;

a cartridge having a flange adapted to fit within said opening, said cartridge having a diameter slightly larger than the smallest lateral dimension on said opening whereby said cartridge has a friction fit with said barrel;

locking means, attached to one end of said cartridge, for locking said cartridge to said barrel adjacent said front end preventing said opening from widening;

an end wall at said front end of said barrel preventing said flange from extending beyond said end wall and having a bearing surface mating with said locking means; and a plunger adapted to slide within said barrel and forced toward said front end.

5. A manual extruding system for use with dental materials comprising:

a front handle;

a back handle pivotally connected to said front handle;

a barrel, said barrel having a front and rear end, said rear end attached to said front handle;

said barrel having an opening adjacent said front end, said opening extending axially partially along said barrel and at a radial depth less than the radius of said barrel;

a cartridge adapted to fit within said opening, said cartridge having a diameter larger than the smallest late:.al dimension on said opening whereby said cartridge has a friction fit with said barrel;

a flange attached to one end of said cartridge, said flange having a first bearing surface that is angularly disposed relative to a line perpendicular to the longitudinal axis of said cartridge;

an end wall at said front end of said barrel preventing said flange from extending beyond said end wall and having a second bearing surface mating with said first bearing surface; and a plunger adapted to slide within said barrel and forced toward said front end by said back handle.

6. A manual extruding system for use with dental materials as in claim 5 wherein:
said first bearing surface is angularly disposed by less than 30 degrees.

7. A manual extruding system for use with dental materials as in claim 5 wherein:
said barrel and said cartridge made of plastic.

8. A manual extruding system for use with dental materials as in claim 5 wherein:
said barrel is made of a flexible plastic having sufficient flexibility to permit said cartridge to be easily forced into said opening.

9. A manual extruder for use with dental materials comprising:
a front handle;
a back handle pivotally connected to said front handle;
a barrel, said barrel having a front and rear end, said rear end attached to said front handle;
said barrel having an opening adjacent said front end, said opening extending axially partially along said barrel and at a radial depth less than the radius of said barrel;
an end wall at said front end of said barrel for preventing a cartridge when placed therein from extending beyond said end wall and having a bearing surface angularly disposed relative to a line perpendicular to the longitudinal axis of said barrel; and
a plunger adapted to slide within said barrel and forced toward said front end by said back handle.

10. A cartridge for use in a manual extruder of dental materials comprising:
a tubular cartridge having an open end and an opposing closed end;
a nozzle angularly extending form said closed end; and
a flange attached to said open end, said flange having a bearing surface closest to said closed end that is angularly disposed toward said closed end relative to a line perpendicular to the longitudinal axis of said cartridge.

* * * * *